United States Patent [19]

Fujishiro et al.

[11] 4,189,355
[45] Feb. 19, 1980

[54] METHOD FOR DETECTION OF FLUCTUATION IN AIR/FUEL RATIO OF AIR-FUEL MIXTURE FED TO INTERNAL COMBUSTION ENGINE

[75] Inventors: Takeshi Fujishiro; Toru Kita, both of Yokohama, Japan

[73] Assignee: Nissan Motor Company, Limited, Yokohama, Japan

[21] Appl. No.: 917,409

[22] Filed: Jun. 21, 1978

Related U.S. Application Data

[62] Division of Ser. No. 746,790, Dec. 2, 1976, abandoned.

[51] Int. Cl.² ............................................. G01N 27/46
[52] U.S. Cl. ................................ 204/1 T; 204/195 S; 123/119 E
[58] Field of Search ........................... 204/15, 195 S; 123/119 E

[56] References Cited

U.S. PATENT DOCUMENTS

| 3,400,054 | 9/1968 | Ruka et al. | 204/195 S |
| 3,691,023 | 9/1972 | Ruka et al. | 204/195 S |
| 3,819,500 | 6/1974 | Van Esdonk et al. | 204/195 S |
| 3,981,785 | 9/1976 | Sandler | 204/1 S |
| 4,005,001 | 1/1977 | Pebler | 204/195 S |

FOREIGN PATENT DOCUMENTS

| 2304464 | 8/1974 | Fed. Rep. of Germany | 204/195 S |
| 2547683 | 5/1976 | Fed. Rep. of Germany | 204/195 S |

*Primary Examiner*—T. Tung

[57] ABSTRACT

A sensor comprises a layer of an oxygen ion conductive solid electrolyte such as stabilized zirconia, two electrode layers of a catalytic metal such as platinum formed porously on both sides of the electrolyte, only one of them formed on first side of the electrolyte layer being directly exposable to an exhaust gas stream, and a gas passage arranged to allow the exhaust gas to contact the other side of the electrolyte layer with a time lag behind the contact of the gas stream with the first side. A fluctuation in the air/fuel ratio of an air-fuel mixture fed to the engine across the stoichiometric ratio can be detected by this sensor since the fluctuation and the aforementioned time lag cause a difference between oxygen partial pressure on one side of the electrolyte layer and that on the other side, resulting in development of an output voltage of the sensor.

8 Claims, 11 Drawing Figures

METHOD FOR DETECTION OF FLUCTUATION IN AIR/FUEL RATIO OF AIR-FUEL MIXTURE FED TO INTERNAL COMBUSTION ENGINE

This is a division of application Ser. No. 746,790, filed Dec. 2, 1976, now abandoned.

This invention relates to an improvement on a method of detecting the air/fuel ratio of an air-fuel mixture consumed in an internal combustion engine by examining the concentration of oxygen in the exhaust gas and a sensor which operates on the principle of solid electrolyte oxygen concentration cell but can produce an electrical signal clearly indicating a variation of the air/fuel ratio across a stoichiometric ratio.

A conventional oxygen sensor which operates on the principle of concentration cell has a layer of solid electrolyte in which oxygen ions work as carriers and two electron conductive electrode layers which are porously formed on both sides of the electrolyte layer. A typical example of the solid electrolyte is zirconia ceramic containing a stabilizing component such as calcia, and the electrode layers are usually made of platinum. The oxygen concentration in a gas, for example exhaust gas of an internal combustion engine, is examined by exposing the two electrode layers of this sensor respectively to the gas subject to examination and a reference gas such as air. Then the sensor develops and electromotive force across the two electrodes according to the difference in oxygen partial pressure between the examined gas and the reference gas. This electromotive force E is determined by the Nernst's equation:

$$E = \frac{RT}{4F} \log_e \frac{P_2}{P_1} = \frac{KRT}{4F} \log_{10} \frac{P_2}{P_1} \quad (1)$$

where R is the gas constant, T represents the absolute temperature, F is the Faraday constant, K is a constant, P represents oxygen partial pressure, and the subscripts 1 and 2 refer to the gas subject to measurement and the reference gas, respectively. Thus the electromotive force E or output voltage of this sensor is in dependence on temperature, so that the electrolyte layer of the sensor should be kept at an elevated temperature in practical operation.

In the exhaust gas of an internal combustion engine which is operated with a hydrocarbon fuel typified by gasoline, carbon monoxide and unburned hydrocarbons react with oxygen remaining in the exhaust gas. Accordingly the following reactions are considered to respectively be in equilibrium states in the exhaust gas.

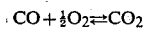

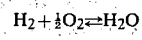

These equilibrium states and, hence, the oxygen partial pressure in the exhaust gas are in dependence on the exhaust gas temperature. Platinum is used as the material of the electrode layers of the sensor partly because of its catalytic ability on these oxidation reactions. Upon contact of the exhaust gas with the platinum electrode, these two reactions rapidly proceed towards the right side. Because of the occurrence of such oxidation reactions on one side of the solid electrolyte layer and a great dependency of the amount of oxygen in the exhaust gas on the air/fuel ratio of the air-fuel mixture consumed in the engine, the described oxygen sensor exhibits the following output characteristic. When the air/fuel ratio is represented by excess air factor λ which can be defined as the ratio of the air-to-fuel ratio of an air-fuel mixture consumed in the engine to the stoichiometric air-to-fuel ratio of the same components, the output voltage of the sensor stands at a relatively high level, only slightly affected by a variation in the air-fuel ratio, (assuming that the exhaust gas temperature does not substantially vary) so long as the value of λ is smaller than 1.0 but stands at a distinctly lower level while λ is larger than 1.0. If the value of λ varies across 1.0, the output voltage exhibits an abrupt transition from one of these two levels to the other.

As is well known, an oxygen sensor of the described type is suitable for use as a detection element in a feedback control system for controlling the air-fuel ratio of an air-fuel mixture fed to an internal combustion engine, particularly, for automotive use in connection with the prevention of air pollution and/or improvement on the fuel economy. The use of this oxygen sensor is especially advantageous when the control system aims at maintaining the excess air factor λ at or in the vicinity of 1.0 as does in many cases. In practical applications, the solid electrolyte layer of this oxygen sensor in most cases is formed into the shape of a tube which is closed at one end for convenience of attachment to, for example, an exhaust pipe for the engine and exposure of only one(outer) side of the electrolyte layer to the exhaust gas.

However, conventional oxygen sensors of the described type have the following disadvantages.

(1) A hermetic and heat-resistant seal is indispensable to the sensors for completely isolating one side of the electrolyte layer from the exhaust gas.

(2) The sensors become inoperable when the solid electrolyte layer, which is not very tough, cracks due to, for example, thermal shocks.

(3) The solid electrolyte layer cannot readily and uniformly be heated to a desirable temperature since the electrolyte layer is heated only from one side.

It is an object of the present invention to provide an improved method of detecting the air/fuel ratio of an air-fuel mixture fed to an internal combustion engine, which method utilizes a sensor operating on the principle of solid electrolyte oxygen concentration cell without involving the above described disadvantages of conventional oxygen sensors.

It is another object of the invention to provide an improved method of detecting the occurrence of a variation in the air/fuel ratio of an air-fuel mixture fed to an internal combustion engine across the stoichiometric air/fuel ratio.

It is still another object of the invention to provide a sensor which operates on the principle of solid electrolyte oxygen concentration cell and is free from the above described disadvantages of conventional oxygen sensors.

It is still another object of the invention to provide a sensor which can produce, when exposed to exhaust gas of an internal combustion engine, an electrical signal clearly indicating a fluctuation in the air/fuel ratio of an air-fuel mixture consumed in the engine across the stoichiometric air/fuel ratio.

An air/fuel ratio detection method according to the invention utilizes a sensor having a layer of an oxygen ion-conductive solid electrolyte and two porous electrode layers of a metal having catalytic ability on oxidation reactions of carbon monoxide and hydrocarbons formed respectively on both sides of the electrolyte layer. The method comprises the steps of contacting a stream of the exhaust gas of an internal combustion engine with first one side of the electrolyte layer of the sensor through the electrode layer formed thereon, and then contacting the same exhaust gas with the other (second) side of the electrolyte layer with a time lag behind the contact of the exhaust gas stream with the first side of the electrolyte layer, so that the sensor produces an output voltage when the air/fuel ratio fluctuates across the stoichiometric ratio and a difference arises between oxygen partial pressure on one side of the electrolyte layer and that on the other side due to both a fluctuation in the oxygen concentration in the exhaust gas stream and the aforementioned time lag.

A sensor according to the invention comprises: a layer of an oxygen ion conductive solid electrolyte; two porous and electron conductive electrode layers of a metal having catalytic ability on oxidation reactions of carbon monoxide and hydrocarbons formed respectively on both sides of the electrolyte layer, only one of the two electrode layers formed on a first side of the electrolyte layer being directly exposable to a stream of gas subject to measurement; and a gas passage arranged to allow the gas to come into contact with the other (second) side of the electrolyte layer with a time lag behind the contact of the gas stream with the first side of the electrolyte layer.

The gas passage of the sensor preferably takes the form of at least one hole formed through the electrolyte layer when the layer has the shape of a tube which is closed at one end, but may alternatively take the form of at least one hole formed through a tubular shell of the sensor particularly when the electrolyte layer has the shape of a disk and is received in the shell to close its one end. The sensor may optionally has a gas outlet for passing a portion of the gas stream to an exterior environment which is substantially at the atmospheric pressure after the contact with the second side of the electrolyte layer.

The air/fuel ratio detection method according to the invention is particularly suitable to an engine system in which the air/fuel ratio is intended to be maintained at or in the vicinity of the stoichiometric air/fuel ratio and has an advantage that, when the air/fuel ratio fluctuates across the stoichiometric ratio, the direction of the fluctuation, that is, whether the fluctuation is from the lower side to the higher side or contrary, can clearly be identified from the polarity of the output voltage of the sensor: the output voltage is a negative one in the former case but positive in the latter case.

The sensor according to the invention has the advantages, besides the described output characteristic, that the sensor can operate even when cracks are present in the electrolyte layer and that the electrolyte layer is heated from both sides and accordingly can readily be heated even under an unfavorable condition as, for example, in cold starting of the engine.

The invention will fully be understood from the following detailed description of preferred embodiments with reference to the accompanying drawings, wherein.

Figure 7:
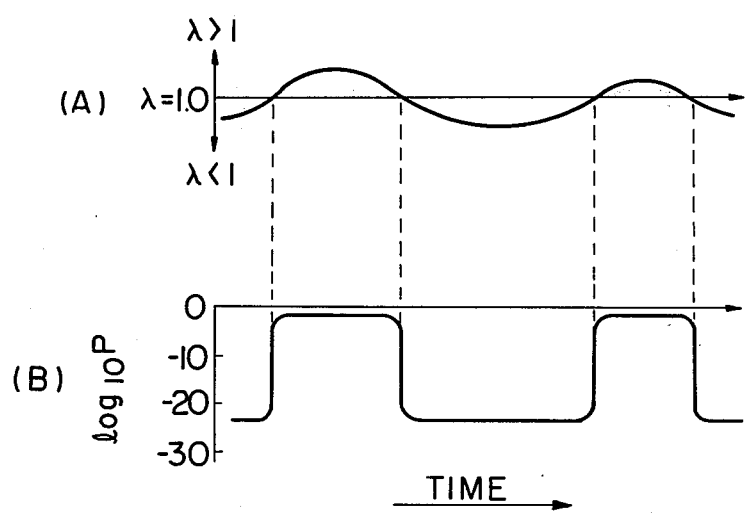
Figure 8:
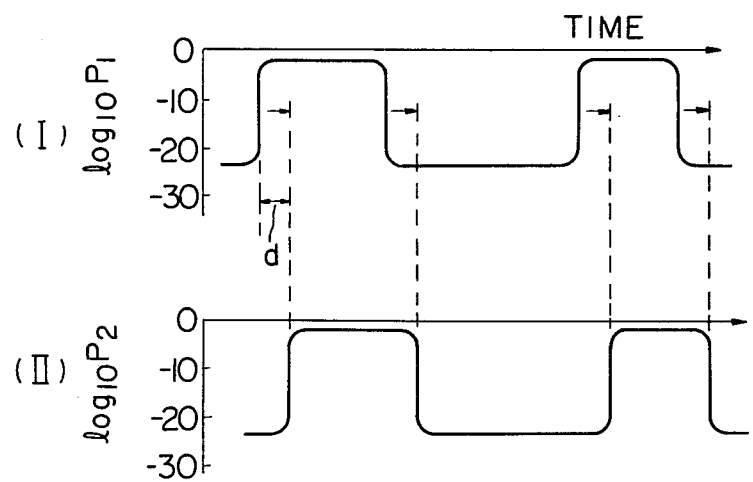
Figure 9:
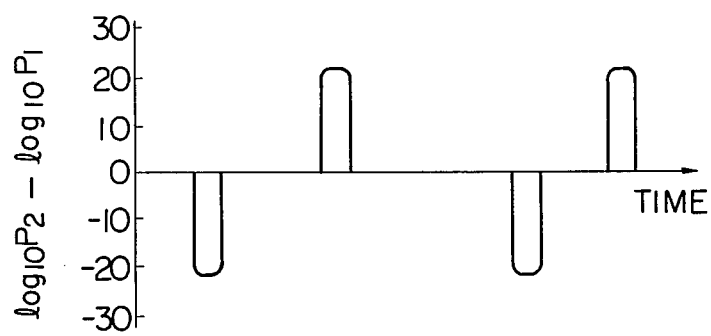
Figure 10:
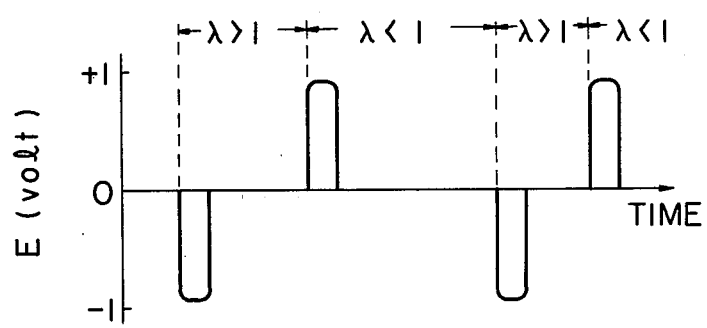
Figure 11:
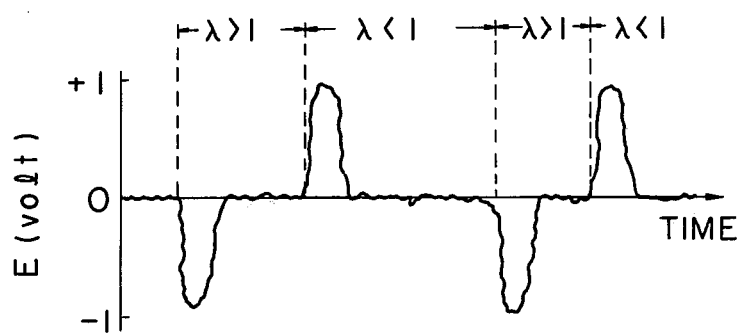

FIG. 7 presents a pair of charts showing a manner of variation in the oxygen partial pressure occurring when the air/fuel ratio exhibits a periodical fluctuation around a stoichiometric ratio;

FIG. 8 presents a pair of charts showing a time lag in the development of an oxygen partial pressure on the inside of a solid electrolyte layer in a sensor according to the invention behind the development of the same oxygen partial pressure on the outside of the same layer;

FIG. 9 is a chart showing a periodical variation in the magnitude of the difference between the oxygen partial pressures on the two sides of the same electrolyte layer derived from the charts of FIGS. 7 and 8;

FIG. 10 is a chart showing a periodical fluctuation in the output voltage of the sensor resulting from the variation shown in FIG. 9; and FIG. 11 is a chart showing the same as FIG. 10 but in a form faithful to an actual function of the sensor in a practical engine system.

Figure 1:
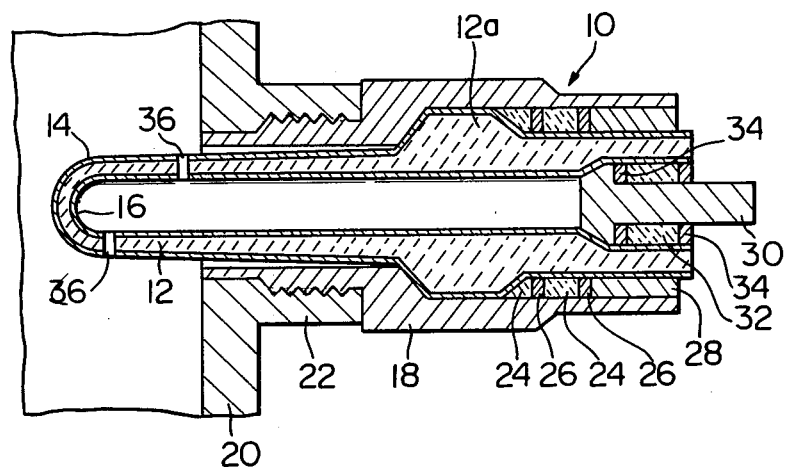
FIG. 1 is a longitudinal sectional view of a sensor as a first embodiment of the invention.

A sensor 10 of FIG. 1 as an embodiment of the invention operates on the known principle of an oxygen concentration cell and has a layer in the form of a tube 12 of an oxygen ion conductive solid electrolyte typified by a zirconia ceramic containing calcia as a stabilizing component. The solid electrolyte tube 12 is closed at one end. The outer surface of this tube 12 is entirely coated with a porous and electron conductive electrode layer 14. This electrode layer 14 is made of a metal such as platinum which has a catalytic activity on the oxidation of oxidizable components of the exhaust gas of an internal combustion engine. The inner surface of the solid electrolyte tube 12 is entirely coated with an electrode layer 16 which is similar to the outer electrode layer 14 both in the material and in the structure.

The outer diameter of the solid electrolyte tube 12 is locally enlarged at a middle section to form an annular ridge or collar 12a. The tube 12 is inserted into a tubular metal shell 18 the inner diameter of which is locally enlarged to fit with the collar 12a of the tube 12 such that a closed end portion of the tube 12 protrudes from the metal shell 18. This metal shell 18. This metal shell 18 has on its outside a fixture means such as threads to airtightly insert the protruded portion of the electrolyte tube 12 into an exhaust pipe 20 for an internal combustion engine, for example, through a boss 22 formed on the wall of the exhaust pipe 20. The metal shell 18 serves also as a conductor for the outer electrode layer 14. The solid electrolyte tube 12 and the metal shell 18 are so shaped as to provide an annular space therebetween at a region from the right side end of the collar 12a to the open end of the electrolyte tube 12. This annular space is filled with a powdery and electrically conductive sealing agent 24 such as, for example, graphite powder, copper powder or semiconductive CuO powder, or a powdery mixture of such a conductive material and a nonconductive and refractory material, which has been compacted in the annular space. To support the compacted sealing agent 24 and fix the electrolyte tube 12 to the metal shell 18, rings 26 of a metal such as copper are forcibly inserted into the annular space. These rings 26 contribute also to the assurance of electrical connection between the outer electrode layer 14 and the metal shell 18. To further assure the fixing of the electrolyte tube 12 to the metal shell 18, a tubular metal retainer 28 is tightly inserted to an open and (right side end) portion of the annular space by means of threads.

An open end portion of the bore of the electrolyte tube 12 is made to have an enlarged diameter with a tapered section, and a metal conductor member 30 which takes the form of a solid cylinder with a tapered flange at one end is partly inserted into the bore of the electrolyte tube 12 such that the tapered flange fits with the tapered section of the bore. The conductor member 30 has such an outer diameter that an annular space is formed between the non-flanged portion of this member 30 and the inner electrode layer 16. This annular space is filled with a powdery and electrically conductive sealing agent 32, which has been compacted and may be of the same material as the sealing agent 24. Metal rings 34 are forcibly inserted into the annular space around the conductor member 30 to support the sealing agent 32 and assure the electrical connection between the inner electrode layer 16 and the conductor member 30.

As an essential feature of a sensor according to the invention, one or a plurality of holes 36 are formed in and through the wall of the solid electrolyte tube 12 and the two electrode layers 14 and 16 at a closed end region protruding from the metal shell 18. These holes 36 are formed usually but not necessarily radially of the tube 12. As the result, the exhaust gas passing through the exhaust pipe 22 can enter the interior of the electrolyte tube 12. However, the cross-sectional area of the holes 36 are small enough to offer a certain resistance to the inflow of the exhaust gas into the interior of the tube 12. Accordingly, the exhaust gas arrives on the inner surface of the electrolyte tube 12 with a certain time lag behind its arrival on the outer surface of the electrolyte tube 12 (both the outer and inner electrode layers 14 and 16 are porous and gas permeable). The interior of the electrolyte tube 12 in the sensor of FIG. 1 is isolated from the atmosphere by the conductor member 30, so that the amount of the aforementioned time lag is determined by the cross-sectional area of the holes 36 and the volume of the interior space defined in the electrolyte tube 12.

Figure 2:
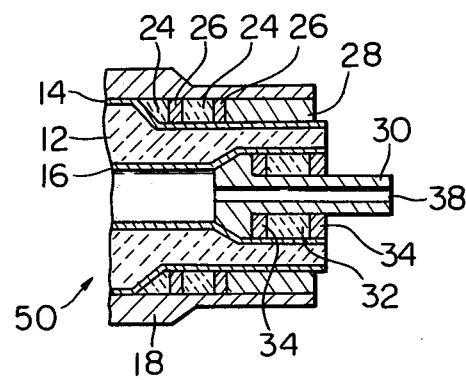
FIG. 2 is a fragmentary and sectional view showing a minor modification of the sensor of FIG. 1.

FIG. 2 shows another sensor 50 as a slight modification of the sensor 10 of FIG. 1. In this case, the conductor member 30 has an axial hole 38 in order to pass therethrough the exhaust gas admitted into the interior of the electrolyte tube 12 into an exterior environment, for example an air cleaner for the engine, which is substantially under the atmospheric pressure. In other respects the sensor 50 of FIG. 2 has the same construction as the sensor 10 of FIG. 1. In this case the amount of the time lag in the arrival of the exhaust gas on the inside of the electrolyte tube 12 behind the arrival on the outside depends on the difference between the exhaust pressure and the atmospheric pressure in addition to the cross-sectional area of the holes 36.

Figure 3:
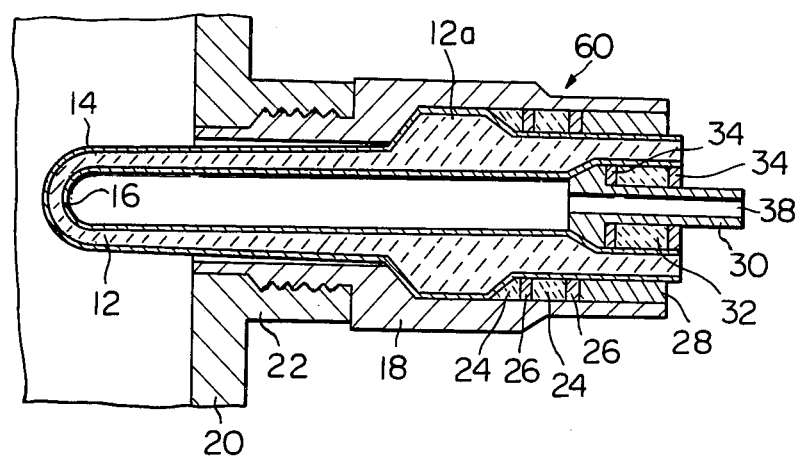
FIG. 3 is a longitudinal sectional view of a conventional oxygen sensor.

A conventional oxygen sensor 60 which is constructed essentially similarly to the sensor 50 of FIG. 2 is shown in FIG. 3. As a sole difference from the sensor 50 of FIG. 2, this conventional oxygen sensor 60 has no holes in the wall of the electrolyte tube 12, because it is necessary for this type of oxygen sensor 60 that the inside of the electrolyte tube 12 is completely isolated from the exhaust gas and is exposed to atmospheric air as a reference gas.

The sensors 10 and 50 are not suitable for exactly measuring the oxygen concentration in the exhaust gas but are quite suitable for examining a fluctuation in the air/fuel ratio of a combustible mixture fed to the engine across the stoichiometric ratio as will be understood from the following explanation of the function of these sensors 10 and 50 in the exhaust gas.

Figure 6:
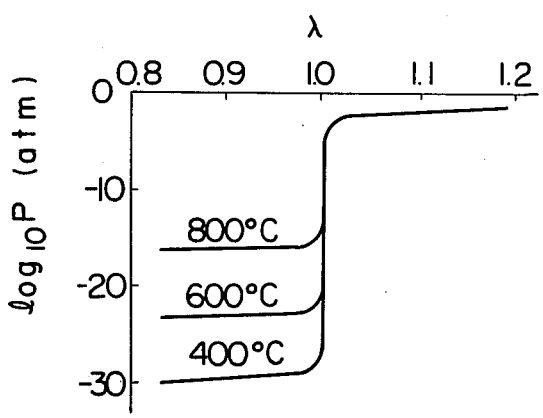
FIG. 6 is a graph showing the relationship between the air/fuel ratio of an air-fuel mixture consumed in an internal combustion engine and the oxygen partial pressure in the exhaust gas of the engine.

When an exhaust gas resulting from the combustion of an air-gasoline mixture in an internal combustion engine is contacted with a catalytic metal such as platinum at a high temperature, an equilibrium partial pressure P(atm) of oxygen in the exhaust gas varies with variations in the air/fuel ratio, i.e. excess air factor $\lambda$, of the mixture and the exhaust gas temperature in a manner as shown in FIG. 6. The oxygen partial pressure P stands at two distinctly different levels according as the value of $\lambda$ remains on either side of 1.0 where the air/fuel ratio is stoichiometric. At 600° C., for example, the oxygen partial pressure P is on the order of $10^{-20}$ while the value of $\lambda$ is smaller than 1.0 but on the order of $10^{-2}$ while $\lambda$ is larger than 1.0. The oxygen partial pressure P exhibits an abrupt transition from one of these two levels to the other when $\lambda$ varies across 1.0.

The operation of a feedback system for maintaining the value of $\lambda$ at 1.0 will result in a small magnitude of periodical fluctuation of the value of $\lambda$ around and across 1.0 as typified by the chart (A) of FIG. 7. On the basis of this chart (A) and the graph of FIG. 6, the oxygen partial pressure P in the exhaust gas (upon contact with platinum) at 600° C. exhibits a periodical fluctuation in a monomer as shown by the chart (B) of FIG. 7.

If the sensor 10 or 50 according to the invention is exposed to a stream of the exhaust gas in which the oxygen partial pressure P fluctuates as shown in FIG. 7, the fluctuating oxygen partial pressure P is applied onto the outside of the electrolyte tube 12 since the exhaust gas can pass through the outer electrode layer 14. For the outside of the electrolyte tube 12, this oxygen partial pressure P will hereinafter be represented by $P_1$ for convenience in explanation. In FIG. 8, the chart (I), which is substantially identical with the chart (B) of FIG. 7, shows the fluctuation in the oxygen partial pressure $P_1$ in the exhaust gas stream on the outside of the electrolyte tube 12. Then the exhaust gas enters the interior of the electrolyte tube 12 through the holes 36 and arrives on the inside of the electrolyte tube 12 through the inner electrode layer 16 with a time lag behind the arrival of the same exhaust gas on the outside of the tube 12. For the inside of the tube 12, the oxygen partial pressure will hereinafter be represented by $P_2$. Since the oxygen partial pressure P or $P_1$ exhibits a periodical fluctuation as shown in the chart (I), $P_2$ exhibits a fluctuation fundamentally in the same manner. However, there is a phase difference between the fluctuation of $P_1$ and that of $P_2$ due to the aforementioned time lag. In contrast to the chart (I), the periodical fluctuation of $P_2$ is shown by the chart (II) in FIG. 8. The magnitude of the phase difference between the curve of the chart (I) and that of the chart (II) or the amount of the time lag between the arrival of the exhaust gas on the outside and inside of the electrolyte tube 12 is indicated at d in FIG. 8.

When the amount of the time lag d (which depends on the design of the holes 36 of the sensor 10 or 50) is appropriately preset in relation to the frequency of the periodical fluctuation in the oxygen partial pressure P or fluctuation in the value of λ, there arises a difference between the magnitudes of $P_1$ and $P_2$ intermittently for certain periods of time as seen in FIG. 8. The EMF or output voltage E of the sensor 10 or 50 is given by the following equation:

$$E = \frac{KRT}{4F} \log_{10} \frac{P_2}{P_1}$$
$$= \frac{KRT}{4F} (\log_{10} P_2 - \log_{10} P_1) \quad (2)$$

The value of $(\log_{10} P_2 - \log_{10} P_1)$ calculated from the charts of FIG. 8 exhibits a periodical fluctuation as shown in FIG. 9.

FIG. 10 shows a similar fluctuation of the output voltage E(volts) as the result of a numerical calculation on the equation (2) based on the chart of FIG. 9. As seen in FIG. 10, the output voltage E of the sensor 10 or 50 takes a value of about −1 volt when the value of λ varies across 1.0 from a smaller range (λ<1.0, meaning the presence of excess fuel in the air-fuel mixture) to a larger range (λ<1.0, meaning shortage of fuel in the air-fuel mixture) but another value of about +1 volt when λ varies across 1.0 from a larger range to a smaller range. The output voltage E remains substantially at zero volt while the value of λ remains either above or below 1.0. The output voltage E varies depending on the exhaust gas temperature as demonstrated in FIG. 6, but exhibits a periodical fluctuation in a manner as shown in FIG. 10 regardless of the exhaust gas temperature so long as the value of λ varies across 1.0. It will be understood that the waveform in FIG. 10 is an idealized one and that an actual waveform of the output voltage E in practical use of the sensor 10 or 50 is somewhat deformed and/or rippled as shown in FIG. 11 because of minute and continual variations in various factors including the value of λ.

In a sensor according to the invention, the solid electrolyte layer does not necessarily take a tubular form as in FIGS. 1 and 2.

Figure 4:
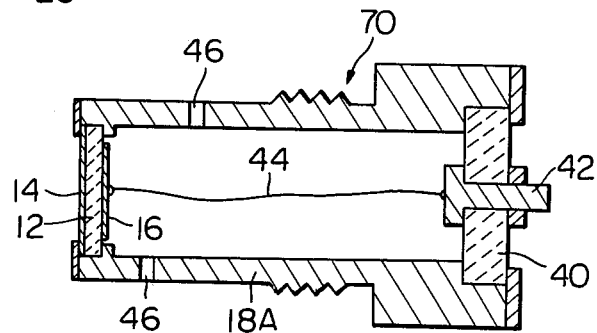
FIG. 4 is a longitudinal sectional view of a sensor as another embodiment of the invention.

Referring to FIG. 4, a sensor 70 as another embodiment of the invention has an oxygen ion conductive solid electrolyte layer 12A which takes the form of a disk and is fixedly and airtightly received in a tubular metal shell 18A to close one end of the shell 18A. The outer and inner electrode layers 14 and 16 are formed on both sides of the electrolyte disk 12A fundamentally in the same manner as in the sensor 10 of FIG. 1. The outer electrode layer 14 is in contact with the metal shell 18A, but the inner electrode layer 16 is isolated from the metal shell 18A. The other end of the tubular shell 18A is airtightly closed by a disk 40 of a heat-resistant and electrically insulating material such as ceramics. A conductor member 42 is passed through and airtightly fixed to the closure disk 40, and a lead 44 of, for example, platinum wire connects the inner electrode layer 16 with the conductor member 42 through the bore of the shell 18A. The shell 18A has threads on its outside and a flange or collar at one end region remoter from the electrolyte disk 12A, so that a portion of the shell 18A including one end closed by the electrolyte disk 12A can be inserted into the exhaust pipe. In this portion, one or a plurality of radial holes 46 are formed in the wall of the shell 18A to serve as a gas passage for admitting the exhaust gas into the interior of the shell 18A with a certain resistance. It will be apparent that the sensor 70 operates in the same manner as the sensor 10 of FIG. 1.

Figure 5:
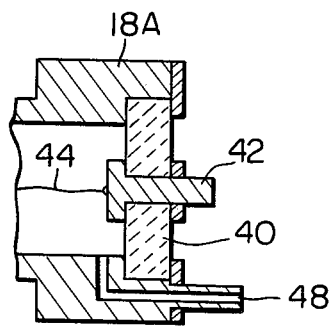
FIG. 5 is a fragmentary and sectional view showing a minor modification of the sensor of FIG. 4.

Substantially similarly to the modification of the sensor 10 of FIG. 1 to the sensor 50 of FIG. 2, the metal shell 18A of the sensor 70 may have a gas outlet hole 48, as shown in FIG. 5, at a location remaining outside of the exhaust pipe.

A sensor according to the invention, regardless of its configuration, may comprise additional components such as, for example, porous protective coatings (not shown) on the surfaces of the outer and/or inner electrode layers 14, 16 and a heat shield member around the shell 18 or 18A as conventional oxygen sensors of the solid electrolyte concentration cell type do.

As will have been understood from the foregoing description, a sensor according to the invention is quite useful as an element of a feedback control system for maintaining the air/fuel ratio of an air-fuel mixture fed to an internal combustion engine exactly at or in the vicinity of a stoichiometric ratio. Compared with the use of a conventional oxygen sensor which is fundamentally constructed as shown in FIG. 3, the method according to the invention has the following advantages.

(1) A sensor according to the invention can operate even if the electrolyte layer cracks due to, for example, thermal shocks.

(2) The solid electrolyte layer can readily and uniformly be heated by the exhaust gas.

(3) The requirement for the hermetic seal is lessned particularly when the inside of the electrolyte layer is isolated from the atmosphere. Besides, it is not necessary to provide any conduit for exposing the inside of the electrolyte layer to air.

(4) It can easily and doubtless be identified whether the amount of fuel in the air-fuel mixture has varied from excess to shortage or contrary since the polarity of the output voltage of the sensor varies depending on the direction of the transition of the air/fuel ratio across the stoichiometric ratio.

What is claimed is:

1. A method of detecting the occurrence of a fluctuation in the air/fuel ratio of an air-fuel mixture fed to an internal combustion engine across the stoichiometric air/fuel ratio, the method comprising the steps of:

disposing a sensor in a stream of the exhaust gas of the engine, said sensor having a layer of an oxygen ion conductive solid electrolyte and porous and electron conductive first and second electrode layers of a metal having catalytic ability on oxidation reactions of carbon monoxide and hydrocarbons contained in the exhaust gas formed respectively on first and second sides of the electrolyte layer, no external voltage being applied to said first and second electrode layers; contacting said stream of the exhaust gas with the first side of said electrolyte layer of said sensor through said first electrode layer;

contacting the exhaust gas with the second side of said electrolyte layer through said second electrode layer with a time lag behind the contact of the exhaust gas with said first side; and detecting the development of a fluctuating electromotive force across said electrolyte layer indicating the existence of a difference between oxygen partial pressure on said first side and oxygen partial pressure on said second side, said difference resulting from the occurrence of a fluctuation in the oxygen concentration in the exhaust gas and the existence of said time lag, whereby the occurrence of said fluctuation in said air/fuel ratio is detected.

2. A method as claimed in claim 1, wherein said sensor takes the form of a tube an end of which is closed by at least a portion of said electrolyte layer with said first side on the outside and has at least one gas-admitting passage formed through the wall of said tube to have a cross-sectional area so small as to offer a substantial resistance to the inflow of the exhaust gas into the interior of said tube and at least one gas-discharging passage.

3. A method as claimed in claim 2, wherein the exhaust gas admitted into the interior of said tube is allowed to flow out of said interior exclusively through said gas-discharging passage.

4. A method as claimed in claim 2, further comprising the step of passing the exhaust gas admitted into the interior of said tube at least partially to an external environment which is substantially at the atmospheric pressure.

5. A method as claimed in claim 1, further comprising the step of identifying whether said fluctuation in the air/fuel ratio across the stoichiometric ratio is a rising fluctuation or contrary based on the fact that said output voltage is a negative one in the case of said rising fluctuation but is a positive one in the case of a lowering fluctuation.

6. A method as claimed in claim 1, wherein said electrolyte layer takes the form of a flat plate fitted in a tubular member so as to close one end of said tubular member with said first side on the outside, said tubular member having at least one gas admitting passage formed through the wall thereof each to have a cross-sectional area so small as to offer a substantial resistance to the inflow of the exhaust gas into the interior of said tubular member and at least one gas-discharging passage formed through said wall.

7. A method as claimed in claim 1, wherein said solid electrolyte is zirconia containing calcia as a stabilizing component.

8. A method as claimed in claim 7, wherein said first and second electrode layers are made of platinum.

* * * * *